United States Patent [19]

Budge et al.

[11] Patent Number: 4,665,042
[45] Date of Patent: May 12, 1987

[54] CATALYSTS FOR THE CONVERSION OF SYN GAS

[75] Inventors: John R. Budge, Cleveland Hts.; Senja V. Compton, Newbury; Gary V. Goeden, North Royalton; Terry J. Mazanec, Solon, all of Ohio

[73] Assignee: The Standard Oil Company, Cleveland, Ohio

[21] Appl. No.: 733,823

[22] Filed: May 14, 1985

[51] Int. Cl.$^4$ .................... B01J 29/04; B01J 29/08; B01J 29/30

[52] U.S. Cl. ........................................ 502/61; 502/66; 502/67; 502/74

[58] Field of Search ...................... 502/67, 74, 66, 61; 208/950; 518/721

[56] References Cited

U.S. PATENT DOCUMENTS

| | | | |
|---|---|---|---|
| 4,011,275 | 3/1977 | Zahner | 208/950 X |
| 4,052,477 | 10/1977 | Ireland et al. | 208/64 X |
| 4,234,412 | 11/1980 | Boersma et al. | 208/950 X |
| 4,260,839 | 4/1981 | Chen et al. | 208/67 |
| 4,279,830 | 7/1981 | Haag et al. | 208/950 X |

Primary Examiner—Carl F. Dees
Attorney, Agent, or Firm—Larry W. Evans; David J. Untener; Raymond F. Keller

[57] ABSTRACT

A catalyst system for the conversion of synthesis gas in a single stage to liquid hydrocarbons comprises
(a) a copper-containing alcohol synthesis catalyst,
(b) an iron-containing modifier for the alcohol synthesis catalyst to promote the formation of hydrocarbons, and
(c) a metallosilicate wax cracking catalyst.

The alcohol synthesis catalyst (a) can contain thorium, zinc, uranium or zirconium in addition to the copper.

The iron-containing modifier (b) can contain an iron-containing zeolite such as ferrierite or an inorganic support containing ferrous or ferric ions. The metallosilicate can be a zeolite or gallosilicate. The zeolite can have a pore diameter of at least 5 Angstroms and can have the faujasite structure. A Group VIIIA metal e.g., Pd may be incorporated on the zeolite to suppress coke formation.

A hydrocarbon product from the conversion can be obtained containing at least 70 percent by weight of hydrocarbons in the range $C_3$ to a boiling point of 340° C., and less than 10 percent by weight of methane.

17 Claims, No Drawings

CATALYSTS FOR THE CONVERSION OF SYN GAS

BACKGROUND OF THE INVENTION

This invention relates to a catalyst system suitable for the conversion of synthesis gas to hydrocarbons, more particularly to a catalyst system comprising a copper-containing component together with an iron-containing component and a wax cracking component such as a Zeolite. This invention also relates to a process for the conversion of synthesis gas to hydrocarbons using the above-described catalyst system.

The conversion of synthesis gas to hydrocarbons by the Fischer-Tropsch process is well known. Usually the catalyst employed in the Fischer-Tropsch process is an iron oxide-containing material although other metal oxides such as those of cobalt, nickel, ruthenium, thorium, rhodium and osmium have been described. However, it is a feature of known Fischer-Tropsch catalysts that a significant proportion of the hydrocarbon product is either in the form of methane and/or wax and this is a disadvantage because the need at the present time is for liquid hydrocarbons suitable for use as transportation fuels.

To reduce the wax content of the product it has been previously proposed to either incorporate with the Fischer-Tropsch catalyst a cracking component such as a Zeolite or to pass the product from the Fischer-Tropsch catalyst over a cracking catalyst in a separate stage.

For example, U.S. Pat. Nos. 4,046,830 and 4,279,830 describe the conversion of synthesis gas to oxygenates and hydrocarbons by first contacting the synthesis gas with a Fischer-Tropsch catalyst in a first stage and then passing the product from the first stage over an acidic crystalline Zeolite in a second stage. The process is operated as two stages because the conditions under which the cracking catalyst is operated are more severe than those required for the hydrocarbon synthesis. It would be an advantage to be able to operate both reactions in a single stage since this would eliminate a reactor vessel and it is an object of the present invention to provide such a process.

U.S. Pat. No. 4,086,262 discloses a process for the conversion of synthesis gas using a single stage process wherein the catalyst is a mixture of (i) a carbon monoxide reducing catalyst such as a methanol catalyst or an iron-containing Fischer-Tropsch catalyst and (ii) a ZSM-5 type Zeolite. However, the products described in this patent contain significant amounts of gaseous hydrocarbons, particularly methane which in all cases exceeds 10 percent by weight of the hydrocarbon product.

It is therefore an object of the present invention to provide a single stage process for the conversion of synthesis gas to hydrocarbons and thereby avoid the disadvantage of the two stages described in U.S. Pat. Nos. 4,046,830 and 4,279,830 and at the same time to produce a hydrocarbon product that either contains less than 10 percent by weight of methane or contains at least 70 percent by weight of hydrocarbons in the range $C_3$ to a boiling point of 340° C.

SUMMARY OF THE INVENTION

According to the present invention, a catalyst system suitable for the conversion of synthesis gas to hydrocarbons comprises the components:
(a) a copper-containing alcohol synthesis catalyst,
(b) an iron-containing modifier for the alcohol synthesis catalyst in an amount to promote the formation of hydrocarbons, and
(c) a metallosilicate wax cracking catalyst in an effective amount to reduce the wax content of the hydrocarbon product.

According to another aspect of the present invention, a process for the conversion of synthesis gas to hydrocarbons comprises contacting synthesis gas at elevated temperature and pressure with a catalyst system comprising the components:
(a) a copper-containing alcohol synthesis catalyst,
(b) an iron-containing modifier for the alcohol synthesis catalyst in an amount to promote the formation of hydrocarbons, and
(c) a metallosilicate wax cracking catalyst.

DETAILED DESCRIPTION OF THE INVENTION

The component (a) of the catalyst system can be any of the copper-containing alcohol synthesis catalysts, for example, a partially reduced mixed metal oxide containing copper and thorium and optionally other metals as disclosed, for example, in U.S. Pat. No. 4,298,354 or a partially reduced mixed metal oxide containing copper and zinc as described in the *Journal of Catalysis* Volume 56, 407–429 (1979) promoted with alkali metal. Other copper zinc catalysts which may be used include (i) copper-zinc oxide-aluminum oxide-potassium catalysts described by C. E. Hofstadt et al in *Preparation of Catalysts III*, page 709, Elsevier Science Publishers BV Amsterdam 1983 (ii) copper-zinc oxide-potassium catalysts described by K. J. Smith et al in the *Canadian Journal of Chemical Engineering* Vol. 61. pages 40–45 (1983) (iii) copper-zinc oxide with alkali or alkaline earth metals described by G. A. Vedage et al in *American Chemical Society Division of Petroleum Chemistry Preprints Washington, D.C. Meeting.* Aug. 29 to Sept. 2, 1983, page 1261.

Further copper-containing alcohol catalysts which may be used include copper zirconium catalysts described in our co-pending patent application U.S. Ser. No. 653,946. Copper beryllium and copper uranium catalysts may also be employed and may be prepared in a manner similar to that described in U.S. Pat. No. 4,298,354 for the copper thorium catalysts or in U.S. Ser. No. 653,946 for the copper zirconium catalysts i.e., by precipitation of the oxides or their precursors from a solution of the metal salts, followed by calcination and partial reduction.

The iron-containing modifier for the alcohol catalyst can be an iron-containing zeolite such as ferrierite or an inorganic oxide support or zeolite exchanged or impregnated with either ferrous or ferric ions.

The purpose of the iron-containing modifier is to alter the products from the reaction from being mainly alcohols to mainly hydrocarbons. Suitable amounts of modifier are such as provides an atomic ratio of iron to copper of at least 0.003 to 1 preferably from 0.03 to 1 to 10 to 1.

Preferably the iron-containing modifier is supported for example on a zeolite which may be naturally occurring such as ferrierite, the iron content of the supported modifier conveniently being from about 0.001 to 80 percent by weight of iron (calculated as metal and based on the weight of the modifier and support) preferably from about 0.5 to 2.0 percent. The supported iron modifier can be prepared by impregnation, ion exchange, coprecipitation or vapor deposition. Naturally occurring iron-containing minerals can be employed.

A preferred support is an inorganic oxide such as silica, titania, magnesia. lanthanum oxide, alumina, a Zeolite or a clay.

The metallosilicate wax cracking catalysts are conveniently zeolite (i.e. an aluminosilicate) wax cracking catalysts which are well known in the art. However, metallosilicates not containing aluminum can be used, for example iron silicates as described, for example. in U.S. Pat. No. 4,350,772 or chromium silicate described, for example in German Offenlegungschrift No. 2831630.

The zeolite preferably has a pore diameter of at least 5 Angstroms, more preferably from about 5 to about 9 Angstroms. The zeolite can be, for example an erionite, offretite, or ferrierite each having a pore diameter of about 5 Angstroms. or mordenite or X zeolite or Y zeolite of the faujasite type each having a pore diameter of about 9 Angstroms, or a zeolite of the ZSM series having an intermediate pore diameter of 5 to 9 Angstroms. Zeolites having pore diameters of from 5 to 9 Angstroms are particularly suitable for obtaining a product containing gasoline. Typical of such zeolites are those of the ZSM series developed by Mobil such as ZSM-5, ZSM-11, ZSM-12, ZSM-21, ZSM-35 and ZSM-38. The silica to alumina ratio is desirably at least 12.

The zeolite cracking catalyst can have Group VIIIA metals such as palladium or platinum added by impregnation or ion exchange to suppress coke formation and can be any of the Group VIIIA metal containing ZSM-5 catalysts described in European Patent Application No. 027,380.

The amount of the cracking catalyst in the catalyst system can vary within wide limits but should preferably be from 20 to 80 percent by weight more preferably 30 to 70 percent by weight of the catalyst system.

The process conditions for the conversion of synthesis gas to hydrocarbons are preferably at temperatures of from 200° C. to 450° C. and pressures of from 1 to 300 atmospheres.

More preferred conditions are a temperature of from 260° C. to 400° C. of from 20 to 75 atmospheres and a gas hourly space velocity of 10 to 100,000, more preferably 500 to 6,000.

The synthesis gas employed in the present invention can contain hydrogen and carbon monoxide in a molar ratio of less than 1:1 particularly less than 1:2, for example from 1:1 to 1:5.

The form of the Periodic Table referred to in the present specification is that published in 1979 by Sargent-Welch Scientific Company of Skokie, Illinois in which the rare gases constitute Group VIII and the iron group metals Group VIIIA.

The invention is illustrated by the following examples. Different catalyst mixtures were prepared, some of which were used with Zeolites.

The catalysts were tested under the conditions set out in Table 1 which also records the results obtained.

Preparation of Catalysts

Preparation A: $Cu_{0.4}ZnO_y$

The procedure follows that described in J Catalysis 56 407–429 (1979).

52.4 g of $Cu(NO_3)_2 \cdot 3H_2O$ (Formula weight 241.6; moles 0.217) and 156 g of $Zn(NO_3)_2 \cdot 6H_2O$ (Formula weight 297.47; moles 0.524) were dissolved in 1500 ml of distilled water. The solution was heated with stirring to between 85° and 90° C., at which temperature a 1 Molar solution of sodium carbonate was added dropwise over a period of one and a half hours (total volume added 500 ml). At this point the precipitate which was initially pale blue became greyish in color. The mixture was allowed to cool over a period of one and a half hours, the precipitate filtered off. washed thoroughly with water and dried in an oven overnight at 110° C. The dried material was placed in an oven set at 200° C. and after one and a half hours the temperature raised to 250° C., after a further half hour to 300° C., after a further half hour to 350° C. and maintained at this temperature for four and a half hours. The material was then allowed to cool and stored in a sealed bottle.

Preparation B: Potassium Doped Catalyst of Formula $Cu_{0.4}Znk_xO_y$ 7.9 g of potassium carbonate ($K_2CO_3$) were dissolved in 100 ml of distilled water. 15 ml of the solution were used to impregnate 10 g of the $Cu_{0.4}ZnO_y$ catalyst prepared in Preparation A. The impregnated catalyst was dried at 120° C. and calcined at 400° C. for six hours. The thus prepared catalyst contained 6.2 percent by weight of potassium.

Preparation C: Sodium Doped Catalyst of Formula $Cu_{0.4}ZnNa_xO_y$ 3.5 g of anhydrous sodium carbonate were dissolved in 90 ml of water and used to impregnate 30 g of the $Cu_{0.4}ZnO_y$ catalyst prepared in Preparation A. The impregnated catalyst was dried at 120° C. and calcined at 400° C. for six hours. The thus prepared catalyst contained 5 percent by weight of sodium.

Preparation D: Pd-Containing Zeolite HLZY62

Zeolite LZY62 (which is an ammonium exchanged Y zeolite obtained from Linde in extrudate form) was converted to its acid form (HLZY62) by calcination at 400° C. 0.4 g of $[Pd(NH_3)_4]Cl_2 \cdot H_2O$ were dissolved in 7 ml of water and the solution used to impregnate 8.9 g of the zeolite HLZY62. The impregnated material was dried in an oven at 120° C. and then calcined at 400° C. for six hours to give a zeolite containing 1 percent Pd.

Preparation E: H Zeolon 700

Zeolon 700 is a natural ferrierite obtained from the Norton Company containing 1 percent by weight of iron. H Zeolon 700 is the acid form of Zeolon 700 and was prepared by exchanging cations in the zeolite with ammonium ions as follows: 1OO g. of Zeolon 700 was added to 500 ml. of a 5 percent (w/v) ammonium chloride solution and the solution stirred for one hour at 95° C. The Zeolite was filtered off and washed. The procedure was repeated 3 more times. The Zeolite was then dried at 120° C. and calcined at 400° C. to convert it to the acid form.

Preparation F: 6.2 Percent Potassium $Cu_{0.4}Zn\ O_y$/H Zeolon 700

10 g of the potassium doped catalyst prepared in Preparation B and 10 g of H Zeolon 700 and 0.8 g graphite were ground together in a McCrone Mill and pressed into pellets, and meshed to between 5 and 30 mesh. then calcined at 400° C. for two hours.

Preparation G: 5 Percent Sodium $Cu_{0.4}Zn\ O_y$/H Zeolon 700

The procedure of Preparation F was followed except 10 g of the sodium doped $Cu_{0.4}Zn\ O_y$ catalyst of Preparation C were used in place of the potassium doped $Cu_{0.4}Zn\ O_y$ catalyst.

Preparation H: 6 Percent Na on $Cu_{1.5}\ Th\ Na_x\ O_y$ Catalyst/H Zeolon 700

125.50 g of $Cu(NO_3)_2 \cdot 2\frac{1}{2}\ H_2O$ and 192.19 g of $Th(NO_3)_4 \cdot 4\ H_2O$ were dissolved in 2.75 liters of distilled water and heated to 90° C. The solution was stirred vigorously and hot aqueous 2M $Na_2\ CO_3$ solution was added slowly over 1¼ hours until the pH was 9.5. The mixture was kept at 90° C. for one hour and then cooled to room temperature. The pH was adjusted to 7.0 with 1.2 M $HNO_3$ and then the mixture vacuum filtered. The filter cake was not allowed to become completely dry and was reslurried with one litre of distilled water and heated to 60° C. then again vacuum filtered.

The filter cake was allowed to dry, was broken up using a pestle and mortar and reslurried with one liter of distilled water again heated to 60° C. and refiltered. The filter cake was dried in an oven at 150° C. for four hours and then calcined in a muffle furnace for 4½ hours at 400° C. This material contained 0.7 percent by weight of sodium.

1.85 g of Na $NO_3$ were dissolved in 4.8 ml of distilled water and the solution used to impregnate 10 g of the above prepared catalyst and dried at 120° C. for two hours. 10 g of the impregnated catalyst containing 6 percent by weight of sodium was mixed with H Zeolon 700 (10 g) and graphite (1 g) and ground using a McCrone Mill. The mixture was pressed into pellets, broken and sieved to collect particles between 5 and 30 mesh, and then calcined at 400° C. for 48 hours.

Preparation I: 4 Percent Na on $Cu_{1.5}\ Th\ Na_x\ O_y$ Catalyst/H Zeolon 700

104.4 g of $Cu(NO_3)_2 \cdot 3\ H_2O$ and 153.8 g of $Th(NO_3)_4 \cdot 4\ H_2O$ were dissolved in 2.5 liters of distilled water. The solution was heated with stirring to about 90° C., then hot 2M $Na_2\ CO_3$ added dropwise over a period of one hour to give a final solution of pH 9.5. The solution was kept at 95° C. for one hour and then allowed to cool to room temperature. The solution was filtered and the filter cake reslurried with one liter of distilled water and heated with stirring to 60°–90° C. for one hour, cooled and filtered again. The filter cake was reslurried as previously described filtered and the filter cake dried at 120° C. in an oven then calcined at 400° C. for four hours. 1.85 g of sodium nitrate were dissolved in 6.6 ml of distilled water and 2.7 ml of this solution used to impregnate 10 g of the above-described catalyst and then the catalyst dried at 120° C. for two hours and calcined at 400° C. for four hours. The calcined catalyst contained 4 percent by weight of sodium, 10 g of which was mixed with 10 g of H Zeolon 700 and 0.8 g graphite and ground together in a McCrone Mill and pressed into pellets, ground and meshed to particles between 5 and 30 mesh and finally calcined at 400° C. for two hours.

Preparation J: 2.4 Percent Na on $Cu_{1.5}\ Th\ Na_x\ O_y$ Catalyst/HZSM35

104.4 g of $Cu(NO_3)_2 \cdot 3\ H_2O$ and 153.8 g of $Th(NO_3)_4 \cdot 4\ H_2O$ were dissolved in 2.5 liters of distilled water and the solution heated with stirring to 90° C. Then 2M $Na_2\ CO_3$ solution was added dropwise over a period of one hour until the pH was 9.5. The solution was kept at 95° C. for one hour and then allowed to cool to room temperature. 2M $HNO_3$ was then added to bring the solution to a pH of 7 and filtered. The filter cake was reslurried in 1200 ml of water, heated to 60° C. and the precipitate allowed to settle. The liquid was decanted off and the volume of the residue made up to 1400 ml with distilled water and heated with stirring to 60° C., then filtered and dried at 120° C. for 48 hours and calcined at 400° C. for four hours. The catalyst contained 2.4 percent by weight of sodium.

10 g of the catalyst and 10 g of zeolite HZSM35 and 0.8 g graphite were mixed, ground in a McCrone Mill, pressed into pellets, broken sieved to between 5 and 30 mesh and calcined at 400° C. for two hours.

HZSM35 was prepared by stirring 50 g of ZSM35 prepared as described in the literature with 25 g of $NH_4$ Cl in 500 ml of water at 85° C. for one hour. The operation was repeated three more times, filtered, washed until washings were free of chloride ions, dried at 125° C. and calcined at 550° C. for six hours to convert to the hydrogen form HZSM35.

Preparation K: 6.7 Percent K on $Cu_{0.4}\ Zn\ K_x\ O_y$ Catalyst/Na Zeolon 700

7.94 g of $K_2\ CO_3$ were dissolved in 100 ml of distilled water and 37.5 ml of this solution were used to impregnate 20 g of the $Cu_{0.4}\ Zn\ O_y$ catalyst which was then dried at 120° C. and then calcined at 400° C. for three hours to yield a catalyst containing 6.7 percent by weight of K. 10 g of the calcined catalyst and 10 g of Na Zeolon 700 from preparation M described below together with 0.8 g of graphite were ground together in a McCrone Mill, pressed into pellets, ground and meshed to between 5 and 30 mesh, then finally calcined at 400° C. for two hours.

Preparation L: 1.8 Percent Pd on HZSM5

HZSM5 was prepared by stirring 50 g of ZSM5 prepared as described in the literature with 25 g of $NH_4$ Cl in 500 ml of water at 85° C. for one hour. The operation was repeated three more times, filtered, washed until washings were free of chloride ions, dried at 125° C. and calcined at 550° C. for six hours to convert to the hydrogen form HZSM5.

0.45 g of $Pd(NH_3)_4\ Cl_2 \cdot H_2O$ were dissolved in 18.4 ml of distilled water and 10 g of the zeolite HZSM5 were impregnated with the solution. 4 g of alumina (Catapal supplied by Conoco Chemicals) were added and thoroughly mixed and the solids pressed into pellets ground and meshed to between 5 and 30 mesh, then dried at 120° C. overnight and calcined at 550° C. for three hours.

Preparation M: Na-Zeolon 700

Zeolon 700 is a natural ferrierite obtained from the Norton Company. H-Zeolon 700, the acid form of Zeolon 700, was prepared first by exchanging cations in the zeolite with ammonium ions as follows: 200 g of Zeolon 700 was added to 1000 ml of a 5 percent (w/v) ammonium chloride solution and the solution was stirred for one hour at 95° C. The zeolite was filtered off and washed. The procedure was repeated three more times. The zeolite was then dried at 120° C. for three hours and calcined at 400° C. for three hours to convert it to the acid form.

84 g of H-Zeolon 700 was added to 1700 ml of a 1 percent (w/v) sodium nitrate solution and the solution was stirred for one hour at 90° C. The zeolite was filtered and washed with 2000 ml distilled water. The zeolite was then dried at 120° C. for two hours and calcined at 400° C. for three hours to form the Na-Zeolon 700.

Preparation N: Cu U $Al_{0.1}$ $O_y$/Na Zeolon 700

217.44 g of $UO_2(NO_3)_2 \cdot 6H_2O$ (formula weight 502.13; moles 0.433), 100.94 g of $Cu(NO_3)_2 \cdot 2\frac{1}{2}H_2O$ (formula weight 232.6; moles 0.434), and 19.69 g $Al(NO_3)_3 \cdot 9H_2O$ (formula weight 375.14; moles 0.053) were dissolved in 2000 ml of absolute methanol. A 2 molar solution of sodium hydroxide in methanol was added dropwise to the nitrate solution while stirring until the pH of the solution reached 7. The slurry was filtered and the filtercake was resuspended in 1000 ml of absolute methanol. The solution was once again filtered and the filtercake resuspended in 1000 ml of absolute methanol. A final filtration was performed with the resultant solids dried in a calcining oven which was programmed to increase from room temperature to 400° C. at 1° C./minute, hold at 400° C. for 120 minutes, and then cool gradually to room temperature. The calcined material was suspended in 1000 ml distilled water. The slurry was stirred for one hour prior to filtration. The filtercake was washed with 300 ml distilled water, then dried in an oven at 120° C. for two hours. Retained sodium was 5.5 percent by weight.

10.38 g of the above prepared catalyst was mixed with 10.36 g of Na-Zeolon 700, and 0.79 g of graphite. The mixture was ground using a McCrone mill with the resultant powder pressed into pellets. The pellets were crushed and sieved to collect particles between 5 and 30 mesh. The particles were then calcined at 400° C. for two hours.

Preparation O: H, LZY-82

Zeolite LZY-82 (which is an ammonium exchanged Y zeolite obtained from Linde in powder form) was pressed into pellets. The pellets were crushed and sieved to collect particles between 5 and 30 mesh. The particles were calcined at 500° C. for two hours to convert the zeolite to its acid form (H, LZY-82).

Preparation P: SK-500

Zeolite SK-500 (which is a rare earth exchanged Y zeolite obtained from Linde in extrudate form) was converted to its active form by calcination at 500° C. for two hours.

Preparation Q: Pd-Containing Zeolite HZSM-11

7.22 g of sodium aluminate was dissolved in 432 ml of a 12 percent tetrapropyl ammonium hydroxide solution at 60° C. This solution was allowed to cool to room temperature prior to the addition of 129.13 g of Ludox AS 40 (colloidal silica dispersion from DuPont) accompanied by vigorous stirring. The resultant viscous mixture was poured into a 2000 ml Teflon liner, which was in turn placed into a stainless steel Parr autoclave. The autoclave was tightly sealed and placed into an oven at 170° C. The autoclave was removed from the oven after three days and quenched in a sink of cold water. After cooling, the autoclave was opened and the solids collected through filtration. The zeolite was washed twice with 800 ml distilled water, dried at 120° C., and calcined at 550° C. for three hours.

The ZSM-11 zeolite was converted to its acid form (HZSM-11) by exchanging cations in the zeolite with ammonium ions as follows: 48 g of ZSM-11 was added to 1000 ml of a 1.1 percent (w/v) ammonium chloride solution and the solution was stirred for one hour at 95° C. The zeolite was filtered off and washed. The procedure was repeated three more times. The zeolite was then dried at 120° C. and calcined at 550° C. for three hours to convert it to the acid form.

0.06 g $Pd(NH_3)_4 Cl_2 \cdot H_2O$ (41.0 percent Pd by weight) was dissolved in 2.5 ml of distilled water and the solution used to impregnate 5.0 g of zeolite HZSM-11 to give a zeolite containing 0.50 percent Pd. The impregnated material was dried in an oven at 120° C. for two hours. 5.00 g of alumina (Catapal SB AL-179-L14 supplied by Conoco) was mixed with the Pd, HZSM-11. The powder was pressed into pellets which were crushed and sieved to collect particles between 5 and 30 mesh. The particles were then calcined at 550° C. for three hours.

Preparation R: $Cu_{1.5}Th\ O_y$ 101.0 g $Cu(NO_3)_2 \cdot 2\frac{1}{2}H_2O$ (formula weight 232.6; moles 0.433) and 158.6 g $Th(NO_3)_4 \cdot 4H_2O$ (formula weight 552.12; moles 0.287) were dissolved in 2000 ml of absolute methanol. A two molar solution of sodium hydroxide in methanol was added dropwise to the nitrate, with stirring, until the pH of the solution reached 7. The slurry was filtered and the filtercake was resuspended in 1000 ml of absolute methanol. The solution was again filtered and the filtercake resuspended in 1000 ml of absolute methanol. A final filtration was performed with the resultant solids dried in a calcining oven programmed to ramp from room temperature to 400° C. at 1° C./min., hold at 400° C. for 120 minutes, and gradually cool to room temperature. The calcined material was suspended in 1000 ml of distilled water and stirred for one hour. The slurry was filtered and the filtercake washed with 300 ml of distilled water. The catalyst was then dried at 110° C.

Preparation S: Sodium Doped Catalyst of Formula $Cu_{0.1}ZrNa_xO_y$

A solution of 50.1 g of zirconium hydroxide (Pflatz and Bauer) suspended in 150 ml of distilled water was refluxed for 24 hours. The solution was filtered and the filtercake was washed with 200 ml of distilled water. The solids were dried at 100° C. for two hours.

2.31 g of $Cu(NO_3)_2 \cdot 2\frac{1}{2}H_2O$ were dissolved in 5 ml of distilled water and the solution used to impregnate 12.2 g of the refluxed zirconia. The impregnated material was dried in an oven at 120° C. for two hours.

1.10 g of sodium carbonate were dissolved in 10 ml of distilled water and the solution used to impregnate 7.96 g of the $Cu_{0.1}ZrO_y$ catalyst. The impregnated material was dried in an oven at 120° C. for two hours to give a catalyst containing 5.9 percent Na and 4.3 percent Cu by weight.

Preparation T: Aluminum Doped Gallosilicate Catalyst 1.70 g of gallium oxide (Aesar) was added to a solution of 5.16 g of sodium hydroxide dissolved in 50.05 g of distilled water. The resultant mixture was heated to 80° C. to insure complete dissolution of the oxide. The solution was filtered and allowed to cool to room temperature. A second solution was prepared by adding 120.86 g of a 20 percent tetrapropyl ammonium hydroxide solution to a mixture of 54.01 g of distilled water and 150.00 g of Ludox AS 40 (colloidal silica dispersion from DuPont). The cooled oxide solution was slowly added to this second solution with rapid stirring. Upon mixing the two solutions, a viscous white gel immediately formed which became mobile with further stirring. After 15 minutes of vigorous stirring, the white paste was poured into the Teflon liner of a 2000 ml stainless steel Parr autoclave. The autoclave was tightly sealed and placed into an oven at 170° C. The autoclave was removed from the oven after four days and quenched in a sink of cold water. After cooling, the autoclave was opened and the solids collected through filtration. The zeolite was washed with 300 ml of distilled water, dried at 120° C., and calcined at 550° C. for three hours.

The gallosilicate zeolite was converted to its acid form ($HGaSiO_x$) by exchanging cations in the zeolite with ammonium ions as follows: 53.35 g of $GaSiO_x$ was added to 1000 ml of a 5 percent (w/v) ammonium chloride solution and the solution stirred for four hours at 80° C. The zeolite was filtered off and dried at 120° C. This procedure was repeated once more with the drying of the zeolite at 120° C. followed by calcination at 550° C. for three hours to convert it to the acid form.

7.56 g of $HGaSiO_x$ were dissolved in 15.23 g of distilled water and the flask was placed on a Rotovapor RE120 unit to achieve constant mixing. A solution of 1.58 g of $Al(NO_3)_3 \cdot 9H_2O$ dissolved in 523.3 g of distilled water was gradually added to the continuously mixed zeolite solution over a three hour period. The aluminum exchanged gallosilicate zeolite collected through filtration was dried at 120° C. for two hours, and then calcined at 550° C. for two hours.

6.61 g of the aluminum exchanged gallosilicate zeolite was mixed with 6.61 g of alumina (Catapal SB AL-179-L14 supplied by Conoco). The powder was pressed into pellets which were crushed and sieved to collect particles between 5 and 30 mesh. The particles were then calcined at 550° C. for two hours.

Preparation U: 2.7 Percent Na on $Cu_{1.5}Th\ O_y$/Na Zeolon 700

0.79 g of sodium carbonate was dissolved in 10 ml of distilled water. 8 ml of the solution were used to impregnate 10.06 g of the $Cu_{1.5}Th\ O_y$ catalyst prepared in Preparation R. The impregnated catalyst was dried at 110° C. for two hours.

The above prepared catalyst was mixed with 11.11 g of Na-Zeolon 700 and 0.89 g of graphite. The mixture was ground using a McCrone mill with the resultant powder being pressed into pellets. The pellets were crushed and sieved to collect particles between 5 and 30 mesh. The particles were then calcined at 400° C. for two hours.

Preparation V: 4 Percent Na on $Cu_{1.5}Th\ O_y$/Na Zeolon 700

0.66 g of sodium carbonate was dissolved in 8 ml of distilled water. This solution was used to impregnate 7.02 g of a $Cu_{1.5}Th\ O_y$ catalyst prepared as in Preparation R. The impregnated catalyst was dried at 120° C. for two hours.

In each case 6.00 g of the above prepared alcohol catalyst was mixed with 5.93 g of Na-Zeolon 700 and 0.61 g of graphite. In every case the mixture was ground using a McCrone mill with the resultant powder pressed into pellets. The pellets were crushed and sieved to collect particles between 5 and 30 mesh. The particles were then calcined at 400° C. for two hours.

Preparation W: 6 Percent Na on $Cu_{0.1}Zr\ O_y$/Na-Zeolon 700

7.21 g of $Cu_{0.1}Zr\ Na_x\ O_y$, as prepared in Preparation S. 7.22 g of Na-Zeolon 700, and 0.82 g of graphite were mixed together. The mixture was ground using a McCrone mill with the resultant powder pressed into pellets. The pellets were crushed and sieved to collect particles between 5 and 30 mesh. The particles were then calcined at 400° C. for two hours.

EXAMPLE 1

The catalyst system employed was a mixture of: (1) 6.2 percent potassium CuOZnO/H Zeolon 700 prepared in Preparation F and (2) 1 percent Pd on zeolite HLZY62 prepared in Preparation D components 1 and 2 being employed in a volume ratio of 4:3 (12 mls and 9 mls respectively) and randomly mixed in the reactor tube. The catalyst was reduced by passing a mixture of hydrogen (20 SCCM) and nitrogen (200 SCCM) in a volume ratio of 1:10 and the temperature raised as follows: 10 minutes to 100° C., two hours 100° to 150° C., two hours 150° to 250° C. and three hours at 250° C. The catalyst was allowed to cool overnight. The catalysts in Examples 2–7 and 10 and 12 were subjected to a similar reduction treatment.

EXAMPLE 2

The catalyst system employed was a mixture of: (1) 5 percent potassium $Cu_{0.4}ZN\ O_y$/H Zeolon 700 prepared in Preparation G and (2) HLZY62 prepared in Preparation D.

Components 1 and 2 were employed in a volume ratio of 4:3, component 1 being added to the reactor tube first and then component 2, the two components being separated by a plug of glass wool.

Experiment A

In Experiment A, no supported iron catalyst was present. The mixture of alcohol catalyst and zeolite used was prepared in Preparation J.

EXAMPLES 3 and 4

In Examples 3 and 4 the iron-containing component and the zeolite cracking catalyst were both provided by the H-Zeolon 700. In Example 4, separate catalyst particles of Zeolite and the modified catalyst were randomly mixed in the reactor tube.

TABLE 1
CATALYST TESTING CONDITIONS AND PRODUCT SELECTIVITIES

| Catalyst System | Example 1 | Example 2 |
|---|---|---|
| Alcohol Catalyst | FROM PREPARATION F | FROM PREPARATION G |
| Supported Fe Zeolite | 1 wt Percent Pd on HLZY62 | HLZY62 |
| Vol ratio of modified catalyst to zeolite | 4:3 | 4:3 |
| GHSV (h$^{-1}$) | 1245 | 1285 |
| Feed H$_2$/CO molar ratio | 0.41 | 0.34 |
| Pressure, (psig) | 750 | 750 |
| Reactor Temperature (°C.) | | |
| Set | 306 | 303 |
| Average Hot Spot | 321 | 325 |
| Run length (hours) | 18.2 | 24.5 |
| Syngas Conversion Percent | | |
| H$_2$ | 59.7 | 60 |
| CO (total) | 33.6 | 33.3 |
| CO to CO$_2$ | 14.9 | 16.0 |
| CO to hydrocarbons | 16.3 | 14.7 |
| CO to oxygenates | trace | trace |
| H$_2$/CO consumption | 0.73 | 0.62 |
| Hydrocarbon Product Distribution Wt Percent | | |
| CH$_4$ | 9.0 | 8.8 |
| C$_2$ | 9.8 | 7.3 |
| C$_3$-C$_4$ | 23.3 | 21.0 |
| gasoline (<180° C.) | 36.7 | 38.0 |
| diesel (<340° C.) | 18.7 | 21.3 |
| Higher MW (>340° C.) | 2.6 | 3.6 |
| Hydrocarbons in the range C$_3$ to a boiling point of 340° C. | 78.7 | 80.3 |

The Table illustrates that in both Examples 1 to 2 a hydrocarbon product was obtained containing less than 10 percent by weight of methane and more than 75 percent by weight of hydrocarbons in the range C$_3$ to a boiling point of 340° C.

TABLE 2
CATALYST TESTING CONDITIONS AND PRODUCT SELECTIVITIES

| Catalysy System | Example 3 | Example 4 | Experiment A |
|---|---|---|---|
| Alcohol Catalyst | FROM PRE-PARATION H | FROM PRE-PARATION I | Cu$_{1.5}$ThNa$_x$O$_y$ (2.4 Wt Percent Na) |
| Supported Fe Zeolite | — | H-zeolon 700 | HZSM35 |
| Vol ratio of modified catalyst to zeolite | — | 1:1 | — |
| GHSV (h$^{-1}$) | 1526 | 2820 | 1545 |
| Feed H$_2$/CO Molar Ratio | 0.57 | 0.63 | 0.62 |
| Pressure, (psig) | 750 | 750 | 750 |
| Reactor Temperature (° C.) | | | |
| Set | 306 | 306 | 349 |
| Average Hot Spot | 358 ± 4 | 327 | 360 |
| Run length (h) | 2.4 | 18.8 | 4.3 |
| Syngas Conversion Percent | | | |
| H$_2$ | 77.4 | 50 | 45.1 |
| CO (total) | 66.4 | 40 | 28.6 |
| CO to CO$_2$ | 29.9 | 20.9 | 9.0 |
| CO to hydrocarbons | 27.8 | 19.1 | 3.2 |
| CO to oxygenates | 2.2 | 1.0 | 9.4 |
| H$_2$/CO consumption | 0.66 | 0.78 | 0.98 |
| Hydrocarbon Product Distribution Wt Percent | | | |
| CH$_4$ | 17.4 | 17.2 | 24.4 |
| C$_2$ | 9.3 | 9.8 | 8.0 |
| C$_3$-C$_4$ | 17.6 | 21.4 | 54.9 |
| gasoline (<180° C.) | 39.5 | 36.6 | 12.7 |
| diesel (<340° C.) | 13.5 | 13.7 | — |
| Higher MW (>340° C.) | 2.7 | 1.3 | — |
| Hydrocarbons in the range C$_3$ to a boiling point of 340° C. | 70.6 | 71.7 | 67.6 |

In Example 3 the catalyst system comprised (1) 6 percent sodium on Cu$_{1.5}$ Th Na$_x$ O$_y$/H Zeolon 700 prepared as described in Preparation H.

In Example 4 the catalyst system comprised (1) 4 percent sodium on Cu$_{1.5}$ Th Na$_x$ O$_y$/H Zeolon 700 as prepared in Preparation I.

This Table shows that for both Examples 3 and 4 the hydrocarbon product contained at least 70 percent by weight of hydrocarbons in the range C$_3$ to a boiling point of 340° C. the amounts being 70.6 and 71.7 for Examples 3 and 4 respectively.

Examples 3 shows that an iron-containing zeolite can be both the iron modifier and the zeolite of the catalyst system.

Experiment A shows that omission of the iron modifier from the catalyst system results in a product in which oxygenates predominate over hydrocarbons and that of the latter the percentage in the range C$_3$ to a boiling pint of 340° C. is below 70.

TABLE 3
CATALYST TESTING CONDITIONS AND PRODUCT SELECTIVITIES

| Catalyst System | Example 5 | Example 6 | Example 7 |
|---|---|---|---|
| Alcohol Catalyst | PREPARED IN PREPARATION K | | |
| Iron Modifier | PREPARED IN PREPARATION M | | |
| Zeolite Wax Cracking Catalyst | PREPARED IN PREPARATION L | | |
| Vol Ratio of Modified Catalyst to Zeolite | 1:3 | 9:7 | 3:5 |
| GHSV (hour$^{-1}$) | 2184 | 2113 | 1820 |
| Feed H$_2$/CO Molar Ratio | 0.44 | 0.41 | 0.42 |
| Pressure psig | 750 | 750 | 750 |
| Reactor Temperature | | | |
| Set | 314 | 315 | 315 |
| Hot Spot | 321 | 321 | 321 |
| Run Length (hours) | 46.3 | 48.2 | 45.4 |
| Synthesis Gas Conversion Percent | | | |
| H$_2$ | 41.5 | 36.9 | 40.9 |
| CO (total) | 22.1 | 24.0 | 25.5 |
| CO to CO$_2$ | 10.7 | 12.4 | 10.4 |
| CO to hydrocarbons | 11.5 | 13.1 | 11.1 |
| CO to oxygenates | trace | trace | trace |
| H$_2$/CO consumption | 0.83 | 0.64 | 0.67 |
| Hydrocarbon Product Distribution, Wt Percent | | | |
| CH$_4$ | 5.8 | 5.0 | 5.8 |
| C$_2$ | 11.2 | 6.5 | 10.5 |
| C$_3$-C$_4$ | 62.1 | 24.2 | 47.3 |
| Gasoline (<180 C.) | 11.4 | 35.9 | 22.5 |
| Diesel (<340 C.) | 3.8 | 10.2 | 4.5 |
| Higher (>340 C.) | 0 | 18.2 | 9.4 |
| Hydrocarbons in the range C$_3$ to | 77.3 | 70.3 | 74.3 |

TABLE 3-continued
CATALYST TESTING CONDITIONS AND PRODUCT SELECTIVITIES

| Catalyst System | Example 5 | Example 6 | Example 7 |
|---|---|---|---|
| a boiling point of 340° C. | | | |

The above examples show that as zeolite content of the catalyst system decreases the yield of higher molecular weight hydrocarbons increases.

EXAMPLE 8

The catalyst system employed was a mixture of: (1) Cu U $Al_{0.1} O_y$/Na-Zeolon 700 prepared in Preparation N and (2) H, LZY-82 prepared in Preparation O. Components 1 and 2 were employed in a volume ratio of 1:1 (9 ml each) and randomly mixed in the reactor tube. The catalyst was reduced by passing a mixture of hydrogen (50 SCCM) and nitrogen (400 SCCM) in a volume ratio of 1:8 over the catalyst bed with the temperature raised as follows: 10 minutes to 100° C., two hours 100° C. to 150° C., two hours 150° C. to 250° C. and three hours at 250° C. The catalysts in Examples 9 and 11 were subjected to a similar reduction treatment.

EXAMPLE 9

The catalyst system employed was a mixture of: (1) 6 percent Na on $Cu_{0.1} Zr O_y$/Na-Zeolon 700 prepared in Preparation W and (2) H. LZY-82 prepared in Preparation O. Components 1 and 2 were employed in a volume ratio of 1:1 (9 ml each) and were randomly mixed in the reactor tube.

EXAMPLE 10

The catalyst system employed was a mixture of: (1) 4 percent Na on $Cu_{1.5} Th O_y$/Na-Zeolon 700 prepared in Preparation V and (2) aluminum exchanged gallosilicate zeolite prepared in Preparation T. Components 1 and 2 were employed in a volume ratio of 1:1 (8.5 ml each) and were randomly mixed in the reactor tube.

EXAMPLE 11

The catalyst system employed was a mixture of: (1) 2.7 percent Na on $Cu_{1.5} Th O_y$/Na-Zeolon 700 prepared in Preparation U and (2) SK-500 prepared in Preparation P. Components 1 and 2 were employed in a volume ratio of 1:3 (4.5 and 13.5 ml respectively) and were randomly mixed in the reactor tube.

EXAMPLE 12

The catalyst system employed was a mixture of: (1) 2.7 percent Na on $Cu_{1.5} Th O_y$/Na-Zeolon 700 prepared in Preparation U and (2) 0.5 percent Pd on H, ZSM-11 prepared in Preparation Q. Components 1 and 2 were employed in a volume ratio of 1:1 (9 ml each) and were randomly mixed in the reactor tube. The catalyst system was reduced as described in Example 1.

The results of Examples 8-12 are summarized in Table 4.

The above described Examples 1-12 illustrate:

(i) The ability of the catalyst system of the present invention to convert synthesis gas having a molar ratio of hydrogen to carbon monoxide of less than one to predominantly liquid hydrocarbons.

(ii) The ability of the catalyst system of the present invention to convert synthesis gas to hydrocarbons in which the hydrocarbon product contains a low quantity of wax (hydrocarbon boiling over 340° C.) and a low quantity of methane.

(iii) As compared with prior references, U.S. Pat. Nos. 4,046,830 and 4,279,830, the catalyst system of the present invention can be used in a single stage to convert synthesis gas to low wax content hydrocarbons.

TABLE 4

| Example | 8 | 9 | 10 | 11 | 12 |
|---|---|---|---|---|---|
| Alcohol Catalyst | Cu O $Al_{0.1} O_x$ | 6.0 Wt. % Na on $Cu_{0.1} Zr O_x$ | 4.0 Wt. % Na on $Cu_{1.5} Th Na_{0.1}O_x$ | 2.7 Wt. % Na on $Cu_{1.5}Th Na_{0.3}O_x$ | 2.7 Wt. % Na on $Cu_{1.5} Th Na_{0.3}O_x$ |
| Iron Modifier | Na-Zeolon 700 | Na-Zeolon 700 | Na-Zeolon 700 | Na-Zeolon 700 | Na-Zeolon 700 |
| Zeolite Waxcracking Catalyst | H,LZY-82 | H,LZY-82 | 0.1 Wt. Al on gallosilicate | SK-500 | 0.5 Wt. Pd on H,ZSM-11 |
| Vol. Ratio of Modified Catalyst to Zeolite | 1:1 | 1:1 | 1:1 | 1:3 | 1:1 |
| GHSV (Hr-1) | 1267 | 1260 | 1263 | 2484 | 1212 |
| Feed $H_2$/CO Molar Ratio | 0.36 | 0.38 | 0.43 | 0.35 | 0.40 |
| Pressure (psig) | 750 | 750 | 750 | 750 | 750 |
| Set Temp. (°C.) | 336 | 339 | 322 | 310 | 320 |
| Hot Spot Temp. (°C.) | 348 | 347 | 335 | 338 | 341 |
| Run Length (Hrs) | 24.0 | 48.4 | 41.5 | 47.0 | 30.9 |
| Synthesis Gas Conversion % | | | | | |
| $H_2$ | 79.3 | 76.9 | 76.1 | 77.1 | 75.1 |
| CO (Total) | 53.5 | 48.0 | 56.0 | 41.4 | 48.8 |
| CO to $CO_2$ | 24.3 | 21.6 | 24.4 | 19.5 | 23.3 |
| CO to Hydrocarbons | 22.8 | 24.3 | 24.3 | 17.7 | 21.7 |
| CO to Oxygenates | trace | trace | trace | trace | trace |
| $H_2$/CO Consumption Ratio | 0.54 | 0.61 | 0.58 | 0.66 | 0.61 |
| Hydrocarbon Product Distrib., Wt. % | | | | | |
| $CH_4$ | 7.9 | 8.8 | 7.3 | 11.1 | 10.6 |
| $C_2$ | 5.9 | 6.4 | 2.3 | 6.7 | 7.5 |
| $C_3$-$C_4$ | 17.8 | 19.7 | 27.6 | 18.2 | 23.7 |
| Gasoline (<180° C.) | 41.5 | 34.5 | 49.8 | 39.0 | 45.5 |
| Diesel (<340° C.) | 17.9 | 16.1 | 10.3 | 14.5 | 5.2 |
| Higher (>340° C.) | 8.9 | 14.4 | 2.8 | 10.5 | 7.5 |
| Hydrocarbons in | 77.2 | 70.3 | 87.7 | 72.7 | 74.4 |

TABLE 4-continued

| Example | 8 | 9 | 10 | 11 | 12 |
|---------|---|---|----|----|----| the range $C_3$ to a boiling point of 340° C.

We claim:

1. A catalyst system suitable for use in the conversion of synthesis gas to hydrocarbons, said catalyst system comprising:
   (a) a copper-containing alcohol synthesis catalyst,
   (b) an iron-containing modifier for the alcohol synthesis catalyst in an amount to promote the formation of hydrocarbons and
   (c) a metallosilicate wax cracking catalyst in an effective amount to reduce the wax content of the hydrocarbon product.

2. The catalyst system as claimed in claim 1 wherein the amount of iron-containing modifier in relation to the copper-containing alcohol synthesis catalyst is such as to provide an atomic ratio of iron to copper of at least 0.003 to 1.

3. The catalyst system as claimed in claim 2 wherein the atomic ratio of iron to copper is from 0.03 to 1 to 10:1.

4. The catalyst system as claimed in claim 1 wherein the alcohol synthesis catalyst contains copper and thorium.

5. The catalyst system as claimed in claim 1 wherein the alcohol synthesis catalyst contains copper and zinc.

6. The catalyst system as claimed in claim 1 wherein the alcohol synthesis catalyst contains copper and zirconium.

7. The catalyst system as claimed in claim 1 wherein the alcohol synthesis catalyst contains copper and uranium.

8. The catalyst system as claimed in claim 1 wherein the metallosilicate is a gallosilicate.

9. The catalyst system as claimed in claim 1 wherein the metallosilicate wax cracking catalyst is a zeolite.

10. The catalyst system as claimed in claim 9 wherein the zeolite is present in an amount from 20 to 80 percent by weight of the catalyst system.

11. The catalyst system as claimed in claim 9 wherein the zeolite is one having a pore diameter of at least 5 Angstroms.

12. The catalyst system as claimed in claim 11 wherein the zeolite is one having the faujasite structure.

13. The catalyst system as claimed in claim 12 wherein the zeolite is an X or Y type zeolite.

14. The catalyst system as claimed in claim 11 wherein the zeolite is a zeolite of the ZSM series.

15. The catalyst system as claimed in claim 11 wherein the zeolite contains an effective amount of a Group VIIIA metal to suppress coke formation.

16. The catalyst system as claimed in claim 1 wherein the iron-containing modifier and the metallosilicate wax cracking catalyst are provided by an iron-containing zeolite.

17. The catalyst system as claimed in claim 16 wherein the iron-containing zeolite is a ferrierite.

* * * * *